United States Patent [19]

Karabin

[11] Patent Number: 5,080,584
[45] Date of Patent: Jan. 14, 1992

[54] METHOD FOR FORMING NICKEL/TITANIUM BRAIDED ARCH WIRES

[75] Inventor: Roger J. Karabin, Plymouth, Conn.

[73] Assignee: Acme-Monaco Corporation, New Britain, Conn.

[21] Appl. No.: 530,641

[22] Filed: May 30, 1990

[51] Int. Cl.[5] ............................................. A61C 3/00
[52] U.S. Cl. ...................................................... 433/20
[58] Field of Search ............................. 433/20, 21, 18

[56] References Cited

U.S. PATENT DOCUMENTS

| Re. 30,332 | 7/1980 | Wallshein |  |
|---|---|---|---|
| Re. 30,593 | 4/1981 | Wallshein |  |
| 3,052,081 | 9/1962 | Wallshein | 433/20 |
| 3,444,621 | 5/1969 | Pletcher | 433/20 |
| 3,729,824 | 5/1973 | Baues et al. |  |
| 3,838,515 | 10/1974 | Paugh et al. |  |
| 4,037,324 | 7/1977 | Andreasen |  |
| 4,182,106 | 1/1980 | Henry | 433/20 |
| 4,186,487 | 2/1980 | Wallshein | 433/20 |
| 4,386,909 | 6/1983 | Hanson | 433/20 |
| 5,018,969 | 5/1991 | Andreiko et al. | 433/20 |

FOREIGN PATENT DOCUMENTS 2814528 10/1978 Fed. Rep. of Germany .

Primary Examiner—Gene Mancene
Assistant Examiner—Michael Lynch

[57] ABSTRACT

An orthodontic arch wire exhibiting relatively constant force over range of deflection of 0.8–1.8 mm and resiliently returnable to its initial position from flexure up to 90° is formed from a braid of nickel/titanium alloy. In the process for making the arch wire, eight strands of the alloy are initially formed into a braid of circular cross section which is then deformed into a rectangular cross section. The deformed braid is wound about a fixture, is heated treated on the fixture and thereafter cut to produce a pair of arch wires from each coil about the fixture. The nickel/titanium alloy is one having a nominal composition of 55% nickel and 45% titanium.

5 Claims, 3 Drawing Sheets

METHOD FOR FORMING NICKEL/TITANIUM BRAIDED ARCH WIRES

BACKGROUND OF THE INVENTION

The present invention relates to orthodontic arch wires and, more particularly, to a method for producing a braided orthodontic arch wire exhibiting substantially constant force over a range of deflection, and to the arch wire produced thereby.

In orthodontic assemblies, generally the practitioner places tooth bands and brackets upon the maloccluded teeth and then forms an arch wire about the brackets to produce a desired force in the direction in which the tooth is to be moved. Desirably, such arch wires will exhibit a level of force sufficient to effect the correction over a period of time without producing too great a discomfort for the patient. In addition, the arch wires should recover from the deflection which is produced for the initial assembly so as to avoid taking a permanent set, i.e., be resiliently deformable within the range required for the installation.

Both single strands and multistrand braids have been used in the fabrication of arch wires. In some instances, the arch wires have also been formed by coiled strands depending upon the alloy employed and the forces desired.

As is known, multiple strand braids offer advantages over single strands. Moreover, it is desirable to use an arch wire with a rectangular cross section to facilitate engagement by the tools and in the brackets.

Exemplary of efforts to produce suitable arch wires are the structures shown in Paugh et al. U.S. Pat. No. 3,838,515, Baues et al. U.S. Pat. No. 3,729,824, Andreason U.S. Pat. No. 4,037,324 and Wallshein U.S. Reissue Pat. Nos. RE. 30,332 and RE. 30,593.

In addition to the desired properties of relatively constant force and a high degree of resilient deformation, the arch wire must be one which can be easily manipulated by the orthodontist, be inert in the patients mouth and be one which can be readily formed into the desired arcuate configuration.

It is an object of the present invention to provide a novel method for fabricating orthodontic arch wires which exhibit relatively constant force over a substantial range of deflection and excellent resilient deformability.

It is also an object to provide such a method which may be easily and economically practiced to produce such arch wires in the desired curvature.

Still another object is to provide a novel braided arch wire of rectangular cross section exhibiting substantially constant force over a relatively broad range of deflection and which will resiliently recover from substantial deformation.

SUMMARY OF THE INVENTION

It has now been found that the foregoing and related objects may be readily attained in a method for making orthodontic arch wires, in which eight-ten strands of substantially circular cross section of an alloy of nickel/titanium alloy are formed into a braid of substantially circular cross section. The circular braid is deformed into a substantially rectangular cross section, and the deformed braid is wound about a fixture with arcuate surfaces of substantially the radius desired for the finished arch wires. The deformed braid on the fixture is heat treated by holding it at a temperature of about 400–600° C. for a period of at least two minutes and thereafter quenching it. After heat treatment the braid is cut at spaced points to produce arch wires of generally arcuate configuration.

Preferably, the alloy has a nominal composition of 55 percent nickel and 45 percent titanium, and the braid is heated to a temperature of at least 200° C. prior to deformation. Desirably, the strands have a diameter of 0.005–0.008 inch and the braid of circular cross section has a diameter of 0.018–0.030 inch.

The fixture has an oval cross section and the braid is cut transversely of the elongate axis of the fixture to produce a pair of wires from each winding thereof. The cut wires are desirably polished.

The resultant orthodontic arch wire comprises a generally arcuate length of a braid of generally rectangular cross section formed from eight-ten strands of a nickel/titanium alloy, and having a cross section of 0.016–0.025 by 0.016–0.030 inch. The arch wire exhibits a relatively constant force over a range of deflection of 0.8–1.8 mm, and resiliently returns to a rest position from flexing of up to 90°. Desirably, the rectangular cross section has a maximum dimension of 0.028 inch, and the surface thereof is polished.

DETAILED DESCRIPTION OF PREFERRED EMBODIMENT OF THE INVENTION

Figure 1:
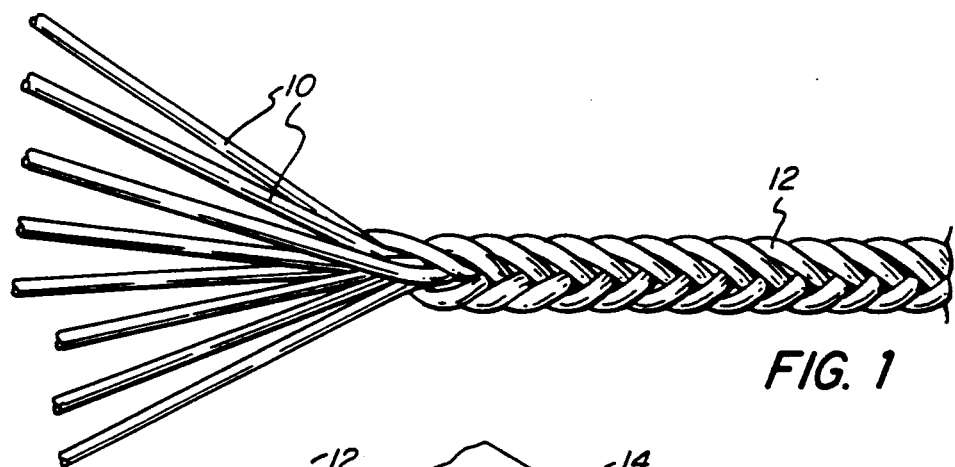
FIG. 1 is a fragmentary view of eight strands of wire as they are being formed into a braid of circular cross section.

Turning first to FIG. 1, there it can be seen that eight strands 10 of wire having a circular cross section are being formed into a braid 12 of circular cross section in a conventional braiding machine (not illustrated).

Figure 2:
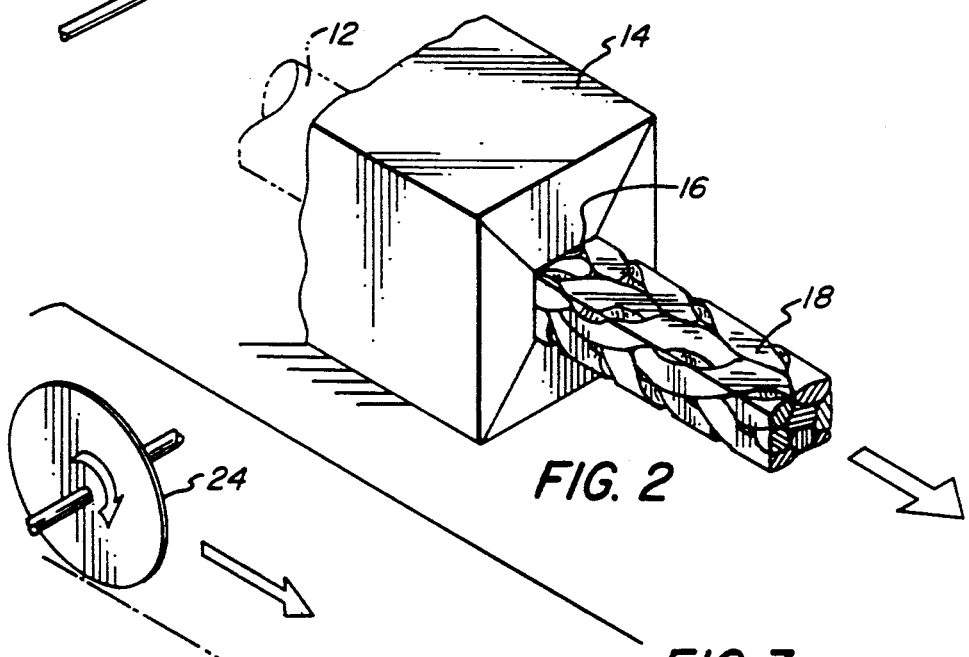
FIG. 2 is a fragmentary perspective view of the braid exiting a die through which it is being drawn to change its cross section from circular to rectangular.
Figure 3:
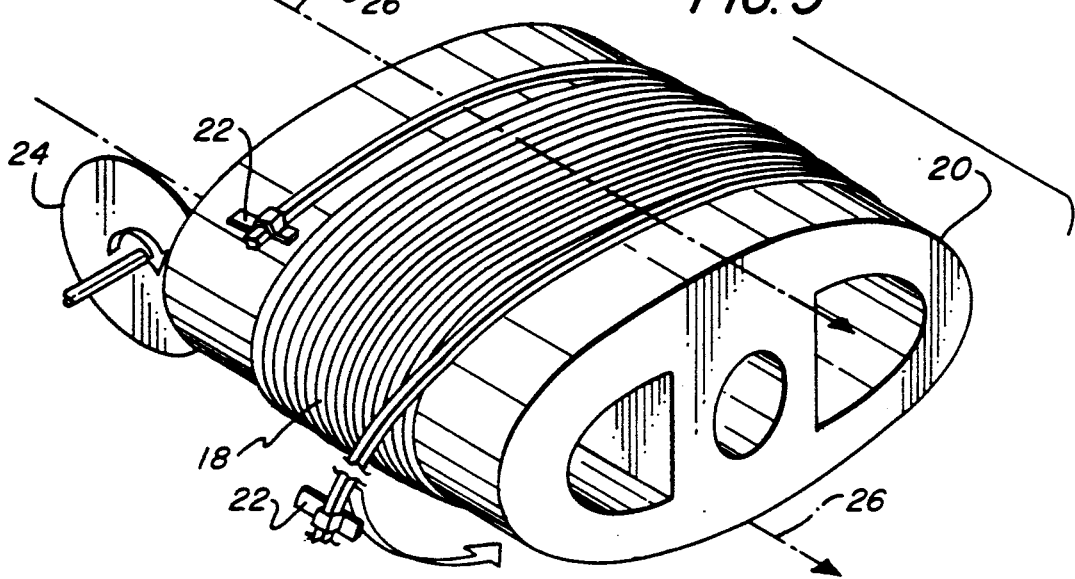
FIG. 3 is a perspective view of a mandrel about which the deformed braid is coiled with one end and its retainer shown as unsecured, and also showing cutter wheels employed to sever the braid after heat treatment to form the desired arch wires.
Figure 4:
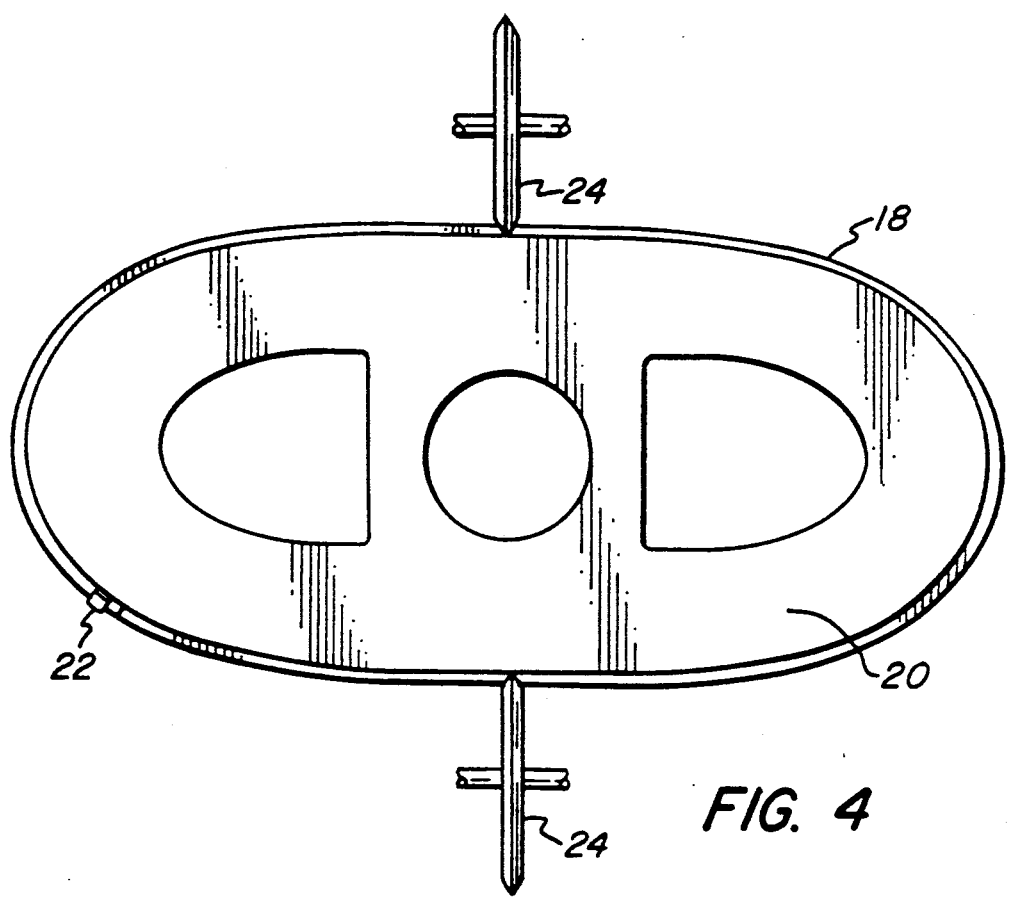
FIG. 4 is a cross sectional view of the mandrel with the braided wire coiled thereabout and showing the cutter wheels cutting the arch wire adjacent the midpoint of the elongate axis of the mandrel.

In FIG. 2, the circular braid 12 formed in FIG. 1 is being pulled through a die 14 which has a passage 16 configured to deform the braid 12 of circular cross section into a braid 18 of rectangular cross section as illustrated.

Following deformation into rectangular cross section, the braid 18 is coiled about a oval mandrel 20 and the ends thereof are secured in retainer elements 22. For convenience, the rotary cutting discs 24 which are used to cut the braid 18 into arch wires following heat treatment are also illustrated in this figure, and their motion across the center of the elongate axis of the mandrel is indicated by the broken lines 26.

Figure 5:
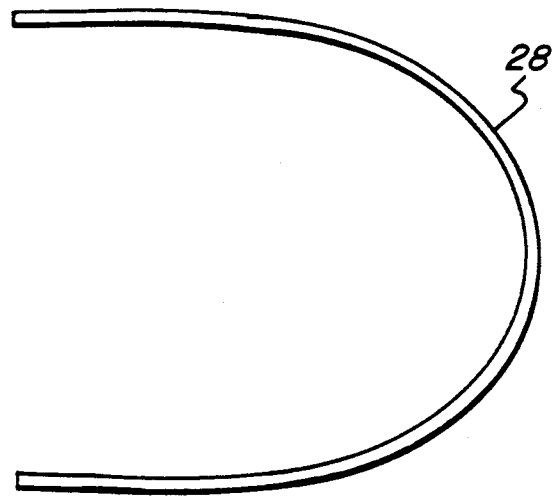
FIG. 5 is a plan view of an orthodontic arch wire produced in accordance with the present invention, and drawn to an enlarged scale relative to FIGS. 3 and 4.

The cutting of the coiled braid produces a pair of arch wires 28 of arcuate configuration from each wrap formed on the mandrel, as seen in FIG. 5.

Figure 6:
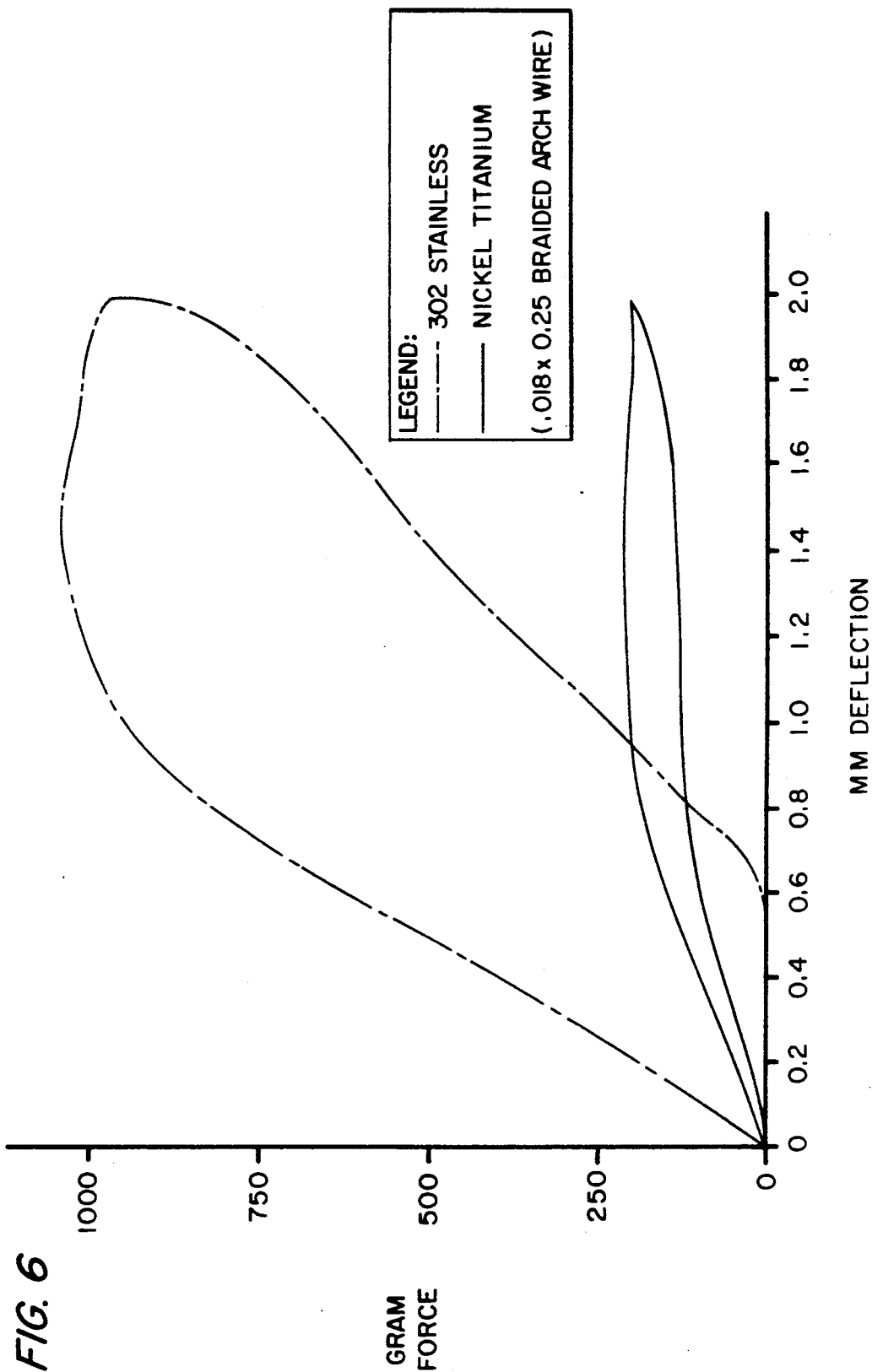
FIG. 6 is a graphic presentation of the force generated by the arch wire of the present invention and one of a stainless steel alloy over a range of deflections.

As seen in FIG. 6, the arch wires produced in accordance with the present invention generate a substantially constant force over a relatively wide useful range of deflection in contrast with the great variation in force provided by the widely employed braided stainless steel arch wires.

Nickel/titanium alloy, having a nominal composition of 55% nickel and 45% titanium has been reported to have excellent resilience, very little tendency to creep, a high degree of biocompatability, and high corrosion resistance. As a result, such alloys have been recommended for medical and dental applications.

By using eight to ten strands of relatively narrow cross section to form a braided structure, a tough, highly resilient braid is obtained. Generally, braids employing eight strands are preferable for the present invention with nine strands being a somewhat less desirable alternative.

To achieve a braided structure which may be handled readily and firmly secured in the orthodontic appliances, the braid is deformed from the circular form in which it is initially created by suitable forming equipment to produce a braid of rectangular cross section. This can be accomplished by roll forming the braid between pairs of cooperating rolls, or by drawing the braid through a die with a passage of suitable configuration to gradually alter the cross section from circular to the desired rectangular form. Although the braid may have a square cross section, generally it is desirable to have a rectangular form in which one transverse dimension side is elongated.

Preferably, the braid is preheated by passing it through a furnace temperature of 900–1000° F. at a rate of about 10–12 feet/minutes, to reduce the energy needed to effect the movement through the forming apparatus.

Following deformation into the rectangular cross section, the braid is wound about a mandrel or other suitable fixture defining the desired contour for the arch wires. As will be appreciated, use of an oval mandrel configured to provide the desired arch wire configuration at both ends of its elongate axis eliminates waste and allows a pair of arch wires to be formed from each wrap on the mandrel by cutting the wrapped wire intermediate the length of the elongated axis, as is illustrated in the attached drawings. As will be appreciated, the radius used to define the arcuate ends will vary for top and bottom arch wires.

To set the braid into the desired configuration defined by the mandrel, the wire on the mandrel is subjected to heat treatment. In this heat treatment, the wire is held at a temperature of about 580–600° C. for a period of about 1–3 minutes following which it is rapidly quenched. Generally the preferred temperature and time for heat treatment is 540° C. and 2 minutes.

Following heat treatment, the wire braid is severed along the elongate axis of the mandrel to form a pair of elements from each wrap of braid on the fixture. In the illustrated embodiment, cutting wheels are shown and these conveniently take the form of narrow grinding discs. If so desired, the fixture may be formed with a recess in its surface to avoid direct contact between the cutting wheels and the body of the fixture. The fixture may be moved relative to the grinding discs, or the opposite technique may be employed, and other cutting techniques may be employed if so desired.

Following the severing of the individual arch wires, they are conveniently polished by tumbling or the like using relatively mild media such as cornmeal. Chemical polishing may also be employed if so desired.

Arch wires produced in accordance with the present invention exhibit extremely desirable uniform force over the range of deflection normally found in orthodontic appliances and they also exhibit excellent resilient recovery from deformation.

Exemplary of the present invention is the following example. A braided arch wire of nickel/titanium alloy was produced by initially braiding eight wires into a circular braid and then passing the wire through cooperating pairs of rolls to produce a rectangular cross section. The initial wire strands were 0.007 inch in diameter, the circular braid was 0.021 inch in diameter and the resultant rectangular braid had dimensions of 0.018×0.025 inch. Prior to deforming the circular braid into the rectangular form, the wire was preheated to a temperature of approximately 200° C.

The wire was then wrapped about an oval fixture substantially as shown in the attached drawings. The fixture or mandrel has an elongate dimension of 5.2 inch and a transverse minor dimension of 3 inch; its surface length was 2 inches. Only a single layer of wire braid is formed on the fixture and there were 350 wraps.

The wire and fixture were then placed in a molten salt bath having a temperature of about 540° C. for a period of two minutes following which the fixture was removed and quenched in cold water. This heat set the braid into the desired configuration.

After cooling, the fixture was placed on a grinding machine and oppose cutoff wheels cut the wire into individual upper arch wires substantially as shown in FIG. 5 and having an elongate dimension of 2.6 inch and a transverse dimension of 2.450 inch between the free ends. The arch wires are burnished in a tumbling machine with cornmeal to remove heat scale media for 4 hours and produce a bright, shiny finish. Because of the high resiliency of the arch wires, they are not deformed during the tumbling operation.

To determine the resilient deformability of the arch wires, specimens were placed in a Tinius Olsen Machine Company stiffness tester. This determines spring back angles after deflection and permanent set angle. The fixed bending span is ½ inch and loads of 0.25 and 0.1 pounds. Tests established that the arch wires of the present invention may be bent to 90° without producing permanent set. In contrast, a stainless steel braided arch wire showed a 9° set after bending to 90° under a 0.25 pound load and a 2° set under a 0.1 pound load changing the bending span to ¼" showed a 0.5° set for the arch wire of the present invention under a 0.25 pound load and a 40° set for the stainless steel arch wire.

To determine the nature of the force exerted by the arch wires upon the customary deformation found in an orthodontic appliance, a three point deflection test is employed. In this test, a length of the heat treated arch wire is supported on two fixed elements of cylindrical cross section having a diameter of 0.062 inch and spaced 0.400 inches apart on centers. A third cylindrical element of the same diameter is moved against the opposite surface of the braid at the center of the span and is coupled to a load cell. As the relative movement of the movable element progresses, the forces generated by the wire as it deflects are measured and recorded. The results of this test are set forth in FIG. 6.

Thus, it can be seen that the method of the present invention rapidly and relatively economically generates arch wires of the desired configuration which exhibit relatively constant force of more comfortable low magnitude over the fairly substantial range of deflection encountered in orthodontic appliances. Moreover, the wires of the present invention recover readily from deflection and do not exhibit permanent set or creep in normal usage. The arch wires may be manipulated readily by the orthodontist and secured firmly in the brackets of the orthodontic appliance.

Having thus described the invention, what is claimed is:

1. In a method for making orthodontic arch wires, the steps comprising:
   (a) providing eight-ten strands of substantially circular cross section of an alloy of nickel/titanium alloy;
   (b) forming said strands into a braid of substantially circular cross section, such braid consisting solely of said strands;
   (c) deforming said braid into a substantially rectangular cross section;
   (d) winding said deformed braid about a fixture of substantially oval cross section providing a pair of elongate arcuate surfaces of substantially the radius desired for the finished arch wires;
   (e) heat treating said deformed braid on said fixture by maintaining it at a temperature of about 400–600° C. for a period of at least two minutes and thereafter quenching it; and
   (f) cutting said deformed and heat treated braid along the length of the fixture at the ends of said arcuate surfaces to produce arch wires of generally arcuate configuration.

2. The method of making orthodontic arch wires in accordance with claim 1 wherein said alloy has a nominal composition of 55 percent nickel and 45 percent titanium.

3. The method for making orthodontic arch wires in accordance with claim 1 wherein said braid is heated to a temperature of at least 200° C. prior to deformation.

4. The method for making orthodontic arch wires in accordance with claim 1 wherein said strands have a diameter of 0.005–0.008 inch and said braid of circular cross section has a diameter of 0.018–0.030 inch.

5. The method for making orthodontic arch wires in accordance with claim 1 wherein said cut wires are polished.

* * * * *